United States Patent
De Lambert et al.

(10) Patent No.: US 9,155,686 B2
(45) Date of Patent: Oct. 13, 2015

(54) DENTAL CEMENT COMPOSITION

(75) Inventors: Bertrand De Lambert, Senlis (FR); Daniel Blanquaert, Paris (FR)

(73) Assignee: S.A.S. CERAVERBIOTECH, Plailly (FR)

( * ) Notice: Subject to any disclaimer, the term of this patent is extended or adjusted under 35 U.S.C. 154(b) by 0 days.

(21) Appl. No.: 13/981,365

(22) PCT Filed: Feb. 3, 2012

(86) PCT No.: PCT/FR2012/050238
§ 371 (c)(1),
(2), (4) Date: Jul. 24, 2013

(87) PCT Pub. No.: WO2012/104563
PCT Pub. Date: Aug. 9, 2012

(65) Prior Publication Data
US 2013/0310481 A1 Nov. 21, 2013

(30) Foreign Application Priority Data
Feb. 3, 2011 (FR) ................................. 11 50866

(51) Int. Cl.
*A61K 6/083* (2006.01)
*A61K 6/06* (2006.01)
*A61K 6/00* (2006.01)
*A61K 6/02* (2006.01)
*C04B 28/04* (2006.01)
*C04B 111/00* (2006.01)

(52) U.S. Cl.
CPC .............. *A61K 6/083* (2013.01); *A61K 6/0008* (2013.01); *A61K 6/024* (2013.01); *A61K 6/0606* (2013.01); *A61K 6/0625* (2013.01); *C04B 28/04* (2013.01); *C04B 2111/00836* (2013.01)

(58) Field of Classification Search
USPC .......................... 423/224; 526/287; 106/606
See application file for complete search history.

(56) References Cited

U.S. PATENT DOCUMENTS

| 5,415,547 | A | 5/1995 | Torabinejad et al. |
| 5,769,638 | A | 6/1998 | Torabinejad et al. |
| 7,575,628 | B2 * | 8/2009 | Lu et al. ........................ 106/640 |
| 8,298,328 | B2 * | 10/2012 | Yang et al. ..................... 106/35 |
| 2010/0139524 | A1 | 6/2010 | Yang et al. |
| 2014/0121280 | A1 * | 5/2014 | Primus et al. ................. 514/635 |

FOREIGN PATENT DOCUMENTS

| EP | 0 899 246 A1 | 3/1999 |
| EP | 1 531 779 B1 | 5/2005 |
| EP | 1531779 | * 1/2010 |
| WO | 2005/039509 A1 | 5/2005 |
| WO | WO 2005-039509 | * 5/2005 |
| WO | 2010/034938 A2 | 4/2010 |

OTHER PUBLICATIONS

International Search Report for PCT/FR2012/050238 dated Aug. 8, 2012.
English translation of the International Preliminary Report on Patentability for PCT/FR2012/050238.

* cited by examiner

Primary Examiner — Marc Zimmer
(74) Attorney, Agent, or Firm — Sughrue Mion, PLLC

(57) ABSTRACT

A dental cement composition comprising more than 50% by weight Portland cement, and characterized in that it further comprises a polymer selected from styrene, vinyl, and acrylic polymers carrying a sulfonate function.

13 Claims, No Drawings

DENTAL CEMENT COMPOSITION

CROSS REFERENCE TO RELATED APPLICATIONS

This application is a National Stage of International Application No. PCT/FR2012/050238 filed Feb. 3, 2012, claiming priority based on French Patent Application No. 1150866 filed Feb. 3, 2011, the contents of all of which are incorporated herein by reference in their entirety.

The present invention relates to a dental cement composition comprising a majority of Portland cement. Such a dental cement composition is used for filling cavities made in teeth, e.g. by drilling, and in particular cavities in the root canal system or in deep caries. Dentists are having ever-greater recourse to such dental cement compositions based on Portland cement since they present good biocompatibility and they provide good sealing, thus forming a barrier against infections generated by microorganisms.

Documents U.S. Pat. No. 5,415,547, U.S. Pat. No. 5,769,638, EP 1 531 779, and WO 2010/034938 are already known in the prior art. In the WO document, the dental cement composition comprises 64% Portland cement (or Portland clinker), 3% natural gypsum, 15% calcium carbonate as a binder, and 18% barium chloride as an opacifier. That dental cement composition is supposed to present an advantage over prior art cement compositions, and in particular concerning a shorter setting time, and mixing and manipulation that are easier. It is also mentioned in that document that that dental cement composition satisfies the properties that are normally required, namely hermetically sealing all cavities, in particular those in the canal system and in deep caries, biocompatibility, stimulating regeneration of periapical tissues, hardening without being affected by moisture, stable in volume, no corrosion or electrochemical activity, no coloring of the tooth nor of adjacent tissues, easy to manipulate clinically, and radiological opacity that is different from that of dentine. Some of those properties are provided by the Portland cement, others, such as radiological opacity, by the barium chloride. The calcium carbonate makes manipulation easy because of its binder properties. Document WO 2010/034938 gives no numerical indication concerning setting time shorter than in the prior art.

It is certain that the setting time, and also the ease of mixing and of manipulation are parameters that are of particular importance for practitioners, namely a dental surgeon or an oral surgeon. The setting time must be reasonable, i.e. considerably less than one hour. Nevertheless, it must not be too short, i.e. less than 5 minutes (min), so as to leave the dentist time to prepare the paste (composition+water) and to fill the cavity in workmanlike manner. Setting time and also mixing and manipulation are parameters that are measurable under normal conditions of plasticity complying with European standards. Mixing and manipulation are parameters perceived by the dentist when manipulating the cement together with water. In order to be able to fill a cavity in workmanlike manner, the paste (composition+water) must neither be too pasty, nor too granular.

An object of the present invention is to define a new dental cement composition that naturally satisfies the requirements of the prior art as listed above and that also makes it possible further to reduce setting time for given plasticity, but without that harming manipulation and mixing.

This object is achieved according to the invention by a dental cement composition comprising at least 50% by weight Portland cement, and characterized in that it further comprises a polymer carrying a sulfonate function. The polymer is selected from styrene, vinyl, and acrylic polymers carrying a sulfonate function. The polymer may be present in the range 0.1% to 25% by weight. Preferably, the polymer is sodium polystyrene sulfonate. In addition to considerably reducing setting time, this polymer provides another advantage associated with the fact that it presents antibacterial, bacteriostatic, and/or antibiotic properties. Consequently it performs two functions, namely that of reducing setting time and an antibacterial function. Good results concerning those two properties have been obtained with sodium polystyrene sulfonate presenting a molecular mass of about 70,000 grams per mole (g/mol), to 500,000 g/mol. The best results have been obtained with the short polymer of 70,000 g/mol.

In addition to Portland cement and the polymer carrying a sulfonate function, the composition may also include gypsum, an opacifier such as $ZrO_2$ or $BaSO_4$, and/or a binder such as a formate, ascorbate, and/or gluconate, e.g. of calcium. Calcium ascorbate is already known and used for treating vitamin C deficiency. Calcium gluconate is already known and used for treating hypocalcemia.

A general formulation for the dental cement composition of the invention may comprise:
- 60% to 95% by weight Portland cement;
- 0.1% to 25% by weight sodium polystyrene sulfonate;
- 0.1% to 5% gypsum;
- 0.1% to 25% $BaSO_4$; and
- 0.1% to 25% calcium formate.

A preferred formulation for the dental cement composition of the invention may comprise:
- 70% to 80% by weight Portland cement;
- 1% to 15% by weight sodium polystyrene sulfonate;
- 2% to 5% gypsum;
- 10% to 25% $BaSO_4$; and
- 1% to 15% calcium formate.

Naturally, instead of sodium polystyrene sulfonate, it is possible in the context of the invention to use a polyvinyl sulfonate or a polyacrylic sulfonate, e.g. of sodium or of some other compatible element.

The spirit of the invention lies in the fact of using a particular polymer that carries a sulfonate function in order to perform two advantageous functions, namely: that of reducing setting time; and also neutralizing or destroying bacteria or microorganisms.

The invention is illustrated below by means of several examples of dental cement compositions, some of which are in accordance with the present invention. The values that are given below are expressed as percentages by weight. Setting times were determined using the NF EN ISO 6876:2003 standard.

EXAMPLE 1

A dental cement composition lying outside the ambit of the invention was made comprising 75.5% Portland cement, 3.5% gypsum, and 21% $ZrO_2$. The plasticity, i.e. the ratio of water to composition was set at 0.37, corresponding to plasticity that is normal relative to the European standards that are in force. The setting time was measured as 48 min. That composition did not contain any polymer carrying a sulfonate function as recommended by the present invention.

EXAMPLE 2

A dental cement composition of the invention was made, comprising 71% Portland cement, 3.2% gypsum and 19.8% $ZrO_2$, 3% calcium ascorbate, and 3% sodium polystyrene sulfonate having a molecular mass of 500,000 g/mol. That composition was mixed with water at a water-to-composition ratio of 0.37, corresponding to plasticity that is normal relative to the European standards that are in force. The setting time was measured as 29 min.

EXAMPLE 3

A dental cement composition of the invention was made comprising 71% Portland cement, 3.2% gypsum and 19.8% $ZrO_2$, 3% calcium gluconate, and 3% sodium polystyrene sulfonate having a molecular mass of 70,000 g/mol. That composition was mixed with water at a water-to-composition ratio of 0.37, corresponding to plasticity that is normal relative to the European standards that are in force. The setting time was measured as 25 min.

EXAMPLE 4

A dental cement composition of the invention was made comprising 71% Portland cement, 3.2% gypsum and 19.8% $ZrO_2$, 3% calcium ascorbate, and 3% sodium polystyrene sulfonate having a molecular mass of 70,000 g/mol. That composition was mixed with water having a water-to-composition ratio of 0.37, corresponding to plasticity that is normal in accordance with the European standards that are in force. The setting time was measured as 14 min.

EXAMPLE 5

A dental cement composition of the invention was made comprising 76.8% Portland cement, 3.2% gypsum and 10% of $BaSO_4$, 10% calcium formate, and no polymer. The composition was mixed with water at a water-to-composition ratio of 0.37, corresponding to plasticity that is normal in accordance with the European standards that are in force. The setting time was measured as 27 min.

EXAMPLE 6

A dental cement composition of the invention was made comprising 86.8% Portland cement, 3.2% gypsum and 10% $BaSO_4$, with no polymer and no binder. That composition was mixed with water at a water-to-composition ratio of 0.35, corresponding to plasticity that is normal in accordance with the European standards that are in force. The setting time was measured as 41 min.

EXAMPLE 7

A dental cement composition of the invention was made comprising 74.8% Portland cement, 3.2% gypsum and 10% $BaSO_4$, 10% calcium formate, and 2% sodium polystyrene sulfonate having a molecular mass of 70,000 g/mol. That composition was mixed with water at a water-to-composition ratio of 0.325, corresponding to plasticity that is normal in accordance with the European standards that are in force. The setting time was measured as 16 min.

It can thus be seen that the dental cement compositions of the invention in Examples 2, 3, and 4 present setting times that are much shorter than the dental cement composition of Example 1 that does not form part of the invention. Example 4 provides the best results in terms of setting time, namely 14 min, which is neither too long nor too short for a dentist.

Examples 5, 6, 7 show that sodium polystyrene sulfonate has a positive effect on setting time, as does the binder (calcium formate). The setting time goes from 41 min without polymer and without binder, to 27 min with binder but no polymer, and then to 16 min with polymer and binder. The setting time can be lowered to about 10 min by reducing the grain size of the components to about 10 micrometers (µm) or less. The grain size of the polymer may possibly be greater, since grinding a polymer into very fine particles can affect its chains. With such a grain size, compression strength values are obtained of the order of 90 megapascals (MPa)±10 MPa, in application of the NF EN ISO 9917-1:2008 standard.

Without going beyond the ambit of the invention, the proportion of Portland cement may lie in the range 60% to 95% by weight, and preferably in the range 70% to 80% by weight, the proportion of sodium polystyrene sulfonate may lie in the range 0.1% to 25% by weight, preferably in the range 1% to 5% by weight, the proportion of gypsum may lie in the range 0.1% to 5% by weight, preferably in the range 1% to 5% by weight, the proportion of $ZrO_2$ may lie in the range 0.1% to 25% by weight, preferably in the range 5% to 15% by weight, and the proportion of calcium gluconate and/or ascorbate may lie in the range 0.1% to 25% by weight, preferably in the range 0.1% to 15% by weight. The gluconate and the ascorbate may be mixed together or used separately. Instead of $ZrO_2$ and/or BSO4, it is possible to use some other opacifier, providing it is compatible and not toxic. In certain formulations, it is possible to envisage doing without gypsum. It is also possible to do without gluconate and/or ascorbate in certain formulations. It is possible to replace gluconate and/or ascorbate with some other binder, providing it is compatible and not toxic, e.g. calcium formate. Sodium polystyrene sulfonate may be replaced by some other polymer that carries the sulfonate function.

A preferred composition comprises 74.8% by weight Portland cement, 3.2% by weight gypsum, 10% by weight calcium formate, 10% by weight $BaSO_4$, and 2% by weight of sodium polystyrene sulfonate having a molecular mass of about 70,000 g/mol. With the exception of the polymer, the grain size of the components is 10 µm or less.

By means of the invention, a dental cement composition is obtained that presents both a short setting time and antibacterial properties.

The invention claimed is:

1. A dental cement composition comprising more than 50% by weight Portland cement and a;
    wherein the polymer is sodium polystyrene sulfonate presenting a molecular mass of about 70,000 grams per mole (g/mol).

2. A composition according to claim 1, comprising 0.1% to 25% by weight of said polymer.

3. A composition according to claim 1, including gypsum.

4. A composition according to claim 1, including an opacifier.

5. A composition according to claim 1, including a binder.

6. A composition according to claim 1, wherein the various ingredients of the composition present a grain size of less than about 10 µm.

7. A composition according to claim 1, presenting a setting time of the order of 10 min and a compression strength of about 90 MPa.

8. A composition according to claim 1, comprising:
    60% to 95% by weight Portland cement;
    0.1% to 25% by weight sodium polystyrene sulfonate;
    0.1% to 5% gypsum;
    0.1% to 25% $BaSO_4$; and
    0.1% to 25% calcium formate.

9. A composition according to claim 1, comprising:
    70% to 85% by weight Portland cement;
    0.1% to 5% by weight sodium polystyrene sulfonate;
    1% to 5% gypsum;

5% to 15% BaSO₄; and 0.1% to 15% calcium formate.

10. The composition according to claim 4, wherein the opacifier is $ZrO_2$ or $BaSO_4$.

11. The composition according to claim 5, wherein the binder comprises at least one of formate, ascorbate, or gluconate.

12. The composition according to claim 5, wherein the binder comprises calcium formate.

13. The composition according to claim 1, wherein the various ingredients of the composition, except for the polymer, have a grain size of less than about 10 μm.

\* \* \* \* \*